United States Patent
Kim

(10) Patent No.: US 7,514,104 B2
(45) Date of Patent: Apr. 7, 2009

(54) COMPOSITION CONTAINING AN EXTRACT OF PERICARPIUM ZANTHOXYLI FOR PROTECTING BRAIN CELLS AND IMPROVING MEMORY

(76) Inventor: Sung Jin Kim, 104/2003, Hanshin Apartment 60, Chongryangri 1-dong, Dongdeamun-Gu, Seoul (KR) 130-775

(*) Notice: Subject to any disclaimer, the term of this patent is extended or adjusted under 35 U.S.C. 154(b) by 0 days.

(21) Appl. No.: 11/283,635

(22) Filed: Nov. 21, 2005

(65) Prior Publication Data

US 2006/0073225 A1 Apr. 6, 2006

Related U.S. Application Data

(63) Continuation of application No. 10/837,882, filed on May 3, 2004, now abandoned, which is a continuation of application No. PCT/KR02/02061, filed on Nov. 6, 2002.

(51) Int. Cl.
A61K 36/00 (2006.01)
A61K 36/67 (2006.01)

(52) U.S. Cl. ........................ 424/725; 424/734

(58) Field of Classification Search ............... None
See application file for complete search history.

(56) References Cited

U.S. PATENT DOCUMENTS

| | | | |
|---|---|---|---|
| 4,816,481 A | | 3/1989 | Takasugi et al. |
| 5,137,912 A * | | 8/1992 | Teng et al. ............ 514/463 |
| 5,562,906 A | | 10/1996 | Terry et al. ............ 424/771 |
| 6,210,680 B1 | | 4/2001 | Jia et al. ................ 424/725 |
| 6,280,751 B1 * | | 8/2001 | Fletcher et al. ........ 424/401 |
| 6,419,950 B2 * | | 7/2002 | Bombardelli et al. ... 424/452 |
| 6,630,176 B2 | | 10/2003 | Li et al. |

FOREIGN PATENT DOCUMENTS

| | | |
|---|---|---|
| CN | 1323590 | 11/2001 |
| EP | 0319058 | 6/1989 |
| EP | 0443848 A1 | 2/1991 |
| EP | 2000169383 | 6/2000 |
| JP | 2000-103718 | 11/2000 |
| JP | 2001-354958 | 12/2001 |
| WO | 97/01968 | 1/1997 |

OTHER PUBLICATIONS

International Search Report for PCT/KR02/02061 (2003).
Hashimoto, K. et al. "Modulatory Effect of Aliphatic Acid Amides from Zanthoxylum Piperitum on Isolated Gastrointestinal Tract". In Planta. Med. Mar. 2001, 67(2); 179-181.
Xiong, Q. et al. "Morphological and Histological Studies of Chinese Traditional Drug 'Hua Jiao' (Pericarpium Zanthoxyli) and it's Allied Drugs". Yao Xue Bao 1991; 26(12); 938-947. (abstract only).
Hashimoto et al., "Studies on Anti-Allergic Components in the Roots of *Asiasarum sieboldi*", Planta Med., vol. 60 (1994), 124-127.
Goodman et al., "Nordihydroguaiaretic acid protects hippocampal neurons against amyloid B-peptide toxicity, and attenuates free radical and calcium accumulation", Brain Research, 654, (1994) 171-176.
Girard et al., "Azelastine protects against CA1 traumatic neuronal injury in the hippocampal slice", European Journal of Pharmacology 300 (1996) 43-49.
Han et al., "Protection of Brain Cells against AMPA-induced damage by Asiasari Radix extracts", Phytother Res. Sep. 2003; 17(8): 882-6.
Han et al., "Memory enhancing actions of Asiasari radix extracts via activation of insulin receptor and extracellular signal regulated kinase (ERK) I/II in rat hippocampus", Brain Research 974 (2003) 193-201.

* cited by examiner

*Primary Examiner*—Christopher Tate
*Assistant Examiner*—Deborah A. Davis
(74) *Attorney, Agent, or Firm*—Heslin Rothenberg Farley & Mesiti P.C.

(57) ABSTRACT

The present invention relates to a composition containing an extract of pericapium zanthoxyli for protecting brain cells and improving memory, and the composition of this invention induces an effect of protecting brain cells for modern people under brain damage that is caused by environmental factors, such as various stresses, drinking and smoking habits, therefore, it can be used for medicines and health supplements inducing an effect of preventing, treating degenerative disorders and improving memory.

27 Claims, 4 Drawing Sheets

COMPOSITION CONTAINING AN EXTRACT OF PERICARPIUM ZANTHOXYLI FOR PROTECTING BRAIN CELLS AND IMPROVING MEMORY

CROSS-REFERENCE TO RELATED APPLICATIONS

This application is a continuation of U.S. Ser. No. 10/837,882 filed May 3, 2004 which is a continuation of International Application serial number PCT/KR02/002061 filed Nov. 6, 2002 and published on May 15, 2003 as WO 03/039570, which claims priority of Korean Application No. 2001-68781 filed Nov. 6, 2001. The entire disclosures of the prior application are incorporated herein by reference.

FIELD OF THE INVENTION

The present invention relates to a composition containing an extract of pericarpium zanthoxyli for protecting brain cells and improving memory.

BACKGROUND OF THE INVENTION

One of important factors causing brain cell damage is glutamate as an amino acid. Glutamate acts primarily through four types of receptors, such as NMDA (N-methyl-D-aspartate) receptor, AMPA (L-α-amino-3-hydroxy-5-methyl-4-isoxazolpropionate) receptor, kainate receptor and 1S,3R-ACPD receptor [Craig C R, Stitzel R E, *Modern Pharmacology with Clinical Applications*, p293-302, 1997]. Under a stimulus such as cerebral ischemia, it reduces oxygen supply on neurons, and as a result increases anaerobic glycolysis, decreases action of ion pump by reducing ATP as an energy source within tissues, and induces depolarization of neuronal cell membranes by increasing the amount of extracellular potassium ion. In this state, it secretes excitatory neurotransmitter and induces brain damage due to activation of NMDA, AMPA and kainate receptors.

Excito-toxicity caused by excitatory neurotransmitter induces cell stresses, and is generally known that it plays an important role in inducing pathological state like neurodegenerative disorders, such as Alzheimer's disease, Parkinson disease, cerebral apoplexy and amyotrophic lateral sclerosis [Haloween, B., Reactive oxygen species and the central nervous system, *J. Neurochem.* 59, p1609-1623, 1992; Coyle, J. T. and Puttfarcken, P., Oxidative stress, glutamate, and neurodegenerative disorders, *Science* 262, p689-695, 1993; Olanow, C. W., A radical hypothesis for neurodegeneration, *Trends Neurosci.* 16, p439-444, 1993]. At times, neurodegenerative disorders in central nervous system accompany the decline of memory and cognitive functions. In particular, dementia, that is a serious problem in modern aging society, is caused by environmental factors such as inheritance, aging, brain damage, smoking and drinking habits, and other complex factors. Hippocampus is mainly damaged, and in general it is closely related to the reduction of acetylcholine content of the brain. At present, for the purpose of increasing acetylcholine content of the brain, acetylcholine esterase inhibitors are generally used for the treatment of Alzheimer's dementia. Besides, a large number of studies for inhibiting this brain damage are in progress [Gagliardi R J, Neuroprotection, excitotoxicity and NMDA antagonists, Arq. *Neuro-Psiquiatr.* P58, 2000], for example, the development of NMDA antagonist, AMPA antagonist, GABA agonist, intracellular calcium reducer, nitric oxide inhibitor, free radical scavenger, sodium channel inhibitor, glutamate free inhibitor, growth factor, acidosis, hypothermia, potassium channel activators, etc. have been tried.

For NMDA antagonists, dozocyilpn (MK 801), selfotel, cerestat, dextmetofan, etc. have been developed, however, a low dosage of these medicines induces changes in perceptual recognition, discomfort, nystagmus, etc., moreover, a high dosage of these shows mental side effects such as excitement, paranoia, illusion. Besides, NBQX has been developed for AMPA antagonist, however, it has a low possibility in practical use for medical treatment due to manifestation of serious nephrotoxicity.

Therefore, the development of brain protective agents having no toxicity is a matter of urgency.

According to recent studies, it has been disclosed that AMPA receptors play an important role in developing Alzheimer's disease since neuronal cell damage caused by activating the AMPA receptors selectively affects basal forebrain cholinergic neurons (BFCNs), which are related to Alzheimer's disease. It has been suggested that development of treatment strategies for Alzheimer's disease can be attempted with the use of AMPA antagonists. [Weiss, J. H. et al., Basal forebrain cholinergic neurons are selectively vulnerable to AMPA/kainate receptor-mediated neurotoxicity, *Neuroscience* 60, p659-664]. Glial cell plays a decisive role in the survival of neurons. In central nervous system under being developed, the glial cell controls precise movement and proliferation of neurons, and after development it takes part in maintaining homeostasis and synaptic plasticity of neurons. Moreover, glial cell contains receptors and neurotransmitters, which can start the message of neurons that is essential for survival and extinction of neurons. As a result, therefore, protecting glial cell from exterior damages is related to plasticity, homeostasis and survival.

Pericarpium zanthoxyli refers to the rind of dried fruits of *zanthoxylum bungeanum Maxim., zanthoxylum schinifolium* Sieb. Et Zucc., and *zanthoxylum piperitum* A. P. DC, which are distributed in Korea, China, etc., for the ingredient it contains (+)-gamma-cadinene, (+)-beta-pinene, (−)-aromadendrene, (−)-isopulegol, (−)-N-acetylanonaine (R-type), (2E, 4E, 8Z, 11E)-2-hydroxy-N-isobutyl-2,4,8,11-tetradecatetraenamide, (2E, 4E, 8Z, 11Z)-2-hydroxy-N-isobutyl-2,4,8,11-tetradecatetraenamide, (2E, 4E, 8E, 10E, 12E)-2-hydroxy-N-isobutyl-2,4,8,10,12-tetradecatetraenamide, 2-trans-6-trans-8-trans-10-trans-2-hydroxy-N-isobutyl-dodeca-2,6,8,10-tetradecatetraenamide, 1,8-cineole, 2-phenylpropane-2-ol, arnottianamide, citronellal, de-N-methylcholerythrine, halopine, hydroxy-α-sanshool, hydroxy-β-sanshool, hydroxy-γ-sanshool, linalool, nerol, piperitone, skimmianine, terpinen-4-ol, zanthoxylin, zanthobungeanine, α-pinene, (+,−)α-sanshool, α-terpineol, α-thujene, β-sanshool, β-sitosterol, γ-sanshool, trans-ocimene, etc. It has been used for cold perspiration in spleen and stomach, cold and painful stomach, diarrhea, chilly waist and knee, indigestion, acute and chronic gastritis, dysentery, toothache, etc. and generally known for antiparasitic and antibacterial effect. [Cheong, Bo-seop and Shin, Min-gyo, *Iconographical Folk Medicine Encyclopedia*, Younglim Co., Ltd. P795-796, 1999; New Oriental Medicine Handbook, Traditional Oriental Medicine Database, Scientific Research Center of Natural Substances, Seoul University, 1999].

Until now, however, there is no report that pericarpium zanthoxyli has an effect of protecting brain cells and improving memory.

The inventors of the present invention have studied for a long time on the materials for inducing an effect of protecting brain cells and improving memory for modern people under brain damage that is caused by environmental factors, such as various stresses, drinking and smoking habits, and have eventually discovered that pericarpium zanthoxyli shows an effect of protecting brain cells and improving memory to complete the present invention. It is an object of the invention to provide pharmaceutical compositions and health supplements showing an effect of protecting brain cells and improving memory.

DISCLOSURE OF THE INVENTION

It is a general object of the invention to provide a pharmaceutical composition containing an extract of pericarpium zanthoxyli for protecting brain cells and improving memory, wherein said extract of pericarpium zanthoxyli is extracted with water, organic solvent, or a mixed solvent in which said water and organic solvent are mixed together.

In the pharmaceutical composition containing an extract of pericarpium zanthoxyli for protecting brain cells and improving memory, it is preferred that it contains 0.5~50-weight % of pericarpium zanthoxyli extract against total weight of the composition.

It is especially preferred that the extract of pericarpium zanthoxyli is obtained by extracting pericarpium zanthoxyli with an organic solvent that is selected from the groups comprising of a low alcohol having 1 to 4 of carbon atom, acetone, chloroform, methylene chloride, ether, ethyl acetate and their mixture.

Preferably, the extract of pericarpium zanthoxyli is obtained by dissolving the extract of pericarpium zanthoxyli obtained according to claim 3 in a mixed solvent of methanol: water, then adjusting to pH 2~4 by adding an acid, and further extracting and fractionating with equal volume of chloroform.

Preferably, the extract of pericarpium zanthoxyli is obtained by dissolving the extract of pericarpium zanthoxyli obtained according to claim 3 in a mixed solvent of methanol: water, adjusting to pH 2~4 by adding an acid, extracting with equal volume of chloroform, then adjusting the fraction that is insoluble in the chloroform to pH 9~12 by adding ammonium hydroxide, and further extracting and fractionating with equal volume of a chloroform:methanol mixed solvent.

Preferably, the extract of pericarpium zanthoxyli is obtained by dissolving the extract of pericarpium zanthoxyli obtained according to claim 3 in a mixed solvent of methanol: water, adjusting to pH 2~4 by adding an acid, extracting with equal volume of chloroform, then adjusting the fraction that is insoluble in the chloroform to pH 9~12 by adding ammonium hydroxide, and extracting with equal volume of chloroform: methanol mixed solvent, and further extracting and fractionating the fraction that is insoluble in the chloroform:methanol mixed solvent with methanol.

Preferably, the extract of pericarpium zanthoxyli is obtained by dissolving the extract of pericarpium zanthoxyli obtained according to claim 3 in a mixed solvent of methanol: water, adjusting to pH 2~4 by adding an acid, extracting with same volume of chloroform, then adjusting the fraction that is insoluble in the chloroform to pH 9~12 by adding ammonium hydroxide, extracting with same volume of chloroform: methanol mixed solvent, and further extracting and fractionating the fraction that has not been soluble in the chloroform: methanol mixed solvent with methanol, and obtaining from the fraction that is insoluble in methanol.

Preferably, the extract of pericarpium zanthoxyli may further contain carriers, excipients, diluents or their mixtures.

Moreover, it is especially preferred that the extract of pericarpium zanthoxyli can be formed for dosage in the type of oral, external, suppository forms or sterile injectable solution.

It is another object of the invention to provide health supplemental foods containing an extract of pericarpium zanthoxyli showing an effect of protecting brain cells and improving memory, and food supplemental additives that are allowable in bromatology.

DETAILED DESCRIPTION OF THE INVENTION

Figure 1A:
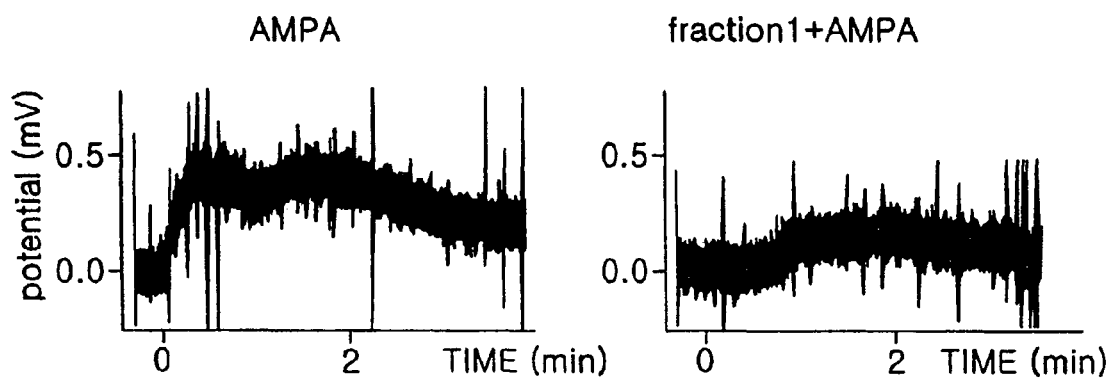
FIG. 1 shows pericarpium zanthoxyli extract (fraction 1) blocking the depolarization induced by AMPA in the rat cortical slices. Data are expressed as mean±standard deviation (n=5). **: $P<0.01$ with respect to the control.

Best Mode for Carrying Out the Invention

According to the above object, this invention provides compositions containing an extract of pericarpium zanthoxyli for protecting brain cells and improving memory.

A composition of this invention for protecting brain cells and improving memory contains 0.5~50-weight % of pericarpium zanthoxyli extract against the total weight of the composition.

An extract of pericarpium zanthoxyli of this invention can be produced through the following processes.

The first step: Pericarpium zanthoxyli is extracted in a low alcohol having 1 to 4 of carbon atom such as methanol, ethanol, or in an organic solvent such as acetone, chloroform, methylene chloride, ether, ethyl acetate, preferably, in methanol or in a mixed solvent of methanol and water within the range of 1:0.2~1.5, at the temperature of 5 to 80° C., preferably, at 30 to 55° C., for the reaction time of 15 min to 48 hours, preferably, 30 min through 12 hours, to obtain a fraction soluble in low alcohol containing a large quantities of terpenoids and phenolic materials.

The second step: The fraction soluble in low alcohol obtained from the above is dissolved in a mixed solvent of low alcohol and water, preferably, in a mixed solvent of methanol and water within the range of 1:0.5~1:1.5, then adjusted to pH 2~4 by adding an acid, and more extracted with equal volume of chloroform to obtain the chloroform fraction of Pericarpium zanthoxyli.

The third step: It is a step to obtain a chloroform:methanol solvent soluble fraction, wherein the fraction that is not dissolved in the above chloroform solvent is adjusted to pH 9-12 with ammonium hydroxide and extracted and fractionated in a mixed solvent with equal volume of chloroform:methanol, preferably, the mixture ratio of chloroform:methanol is within the range of 1:0.1~1. Among the fractions that are not soluble in the chloroform, the fraction soluble in the mixed solvent of chloroform:methanol during the subsequent extraction contains mostly alkaloids, and also, among the fractions that are insoluble in the mixed solvent of chloroform:methanol, the fraction soluble in methanol contains quaternary alkaloids and N-oxides.

The fourth step: The fraction that is insoluble in the mixed solvent of chloroform:methanol is subsequently subjected to extraction with methanol to obtain a methanol soluble fraction and a water-soluble fraction that is insoluble in methanol.

The invention provides compositions for protecting brain cells and improving memory containing low alcohol soluble fraction, chloroform soluble fraction, chloroform:methanol soluble fraction, methanol soluble fraction and water soluble fraction obtained from the above steps.

Moreover, for the extract of pericarpium zanthoxyli of the invention, additional fractionating processes can be performed. [Harborne J. B., Phytochemical methods: *A guide to modern techniques of plant analysis*, 3rd ed., pp6-7, 1998].

The compositions containing pericarpium zanthoxyli extract of the invention may further contain proper carriers, excipients and diluents according to general methods.

As for the carriers, excipients and diluents that can be contained in the compositions containing pericarpium zanthoxyli extract of the invention, there are lactose, dextrose, sucrose, sorbitol, mannitol, zylitol, erythritol, maltitol, starch, acacia rubber, alginate, gelatin, calcium, phosphate, calcium silicate, cellulose, methyl cellulose, microcrystalline cellulose, polyvinyl-pyrrolidon, water, methylhydroxybenzoate, propylhydroxybenzoate, talc, magnesium stearate and minerals.

The compositions containing pericarpium zanthoxyli extract of the invention can be formed for dosage in the type of oral, external, suppository forms and sterile injectable solution, such as powder, tablet, capsule, suspension, emulsion, syrup, aerosol, etc.

The dosage of pericarpium zanthoxyli extract can be varied according to the age, sex, weight of a patient, however, the amount of 0.1 to 500 mg/kg can be administered daily once or several times. The dosage of pericarpium zanthoxyli extract can be increased or decreased according to administration route, degree of disease, sex, weight, age, etc. Therefore, the above dosage should not restrict the scope of this invention in any way.

The compositions containing pericarpium zanthoxyli extract of the invention can be used in medicines, foods and drinks, etc. for protecting brain cells and improving memory in the type of above dosage forms. As for foods to which pericarpium zanthoxyli can be added, for example, there are various foods, drinks, gums, teas, vitamin complexes, health supplemental foods, etc.

Pericarpium zanthoxyli itself of this invention is a medicine that is safe for a long-term dose, since there is little toxicity and side effects in it.

The pericarpium zanthoxyli of this invention can be added to foods or drinks for the purpose of protecting brain cells and improving memory. As for the amount of pericarpium zanthoxyli in foods or drinks, 0.1 to 15 weight % of total weight of food can be generally added, preferably, 1 to 10 weight %, for health supplemental foods, and the rate of 1~30 g, preferably, 3~10 g per 100 ml can be added to health supplemental drinks.

For the composition of health drinks of this invention, there is no special restriction on the liquid components except containing the specified rate of pericarpium zanthoxyli for essential ingredients, and additional components such as various flavorings or natural carbohydrates can be contained as general drinks.

As for the examples of natural carbohydrates described above, there are monosaccharides, e.g., glucose, fructose; disaccharides e.g., maltose, sucrose; and polysaccharides e.g., general sugar such as dextrin, cyclodextrin, and sugar alcohol such as xylitol, sorbitol, erythritol. As for further flavorings, natural flavorings (taumatine, stevia extract such as rebaudioside A, glycyrrhizin) and complex flavorings (saccharin, aspartame, etc.) can be used favorably. The rate of the natural flavorings is generally about 1~20 g, preferably, about 5~12 g per 100 ml of the composition of this invention.

Besides, the composition of this invention can contain various nutriments, vitamins, minerals (electrolytes), flavorings such as complex or natural flavorings, colorants and fillers (cheese, chocolate, etc.), pectic acids and their bases, organic acids, protective colloid thickeners, pH regulators, stabilizers, preservatives, glycerins, alcohols, carbonators that are used in carbonated drinks, etc. Moreover, the composition of this invention can contain fruit fleshes for producing natural fruit juices, fruit juice drinks and vegetable drinks. These components can be used independently or mixedly. The rate of these additives is not so significant, but it is generally selected in the range of 0 to about 20 per the weight 100 of composition of this invention.

This invention will be described more in detail based upon the following examples. However, they will not restrict the present invention.

THE FIRST EXAMPLE

Production of an Extract of Pericarpium Zanthoxyli 250 g of pericarpium zanthoxyli is cut and extracted 3 times in 70% methanol (750 ml) using Soxhlet apparatus. Filtering the extract, it is vacuum concentrated using rotary evaporator (EYELA N-N series) and freeze dried to obtain 16 of methanol crude extract (fraction 1).

To fractionate 10 g of the freeze dehydrated methanol extract in a different organic solvent, it is dissolved in the 200 ml of methanol:water (4:1), adjusted to pH 3 with 2M sulfuric acid, extracted 3 times continuously in the same quantities of chloroform, and it is vacuum concentrated and freeze dried for obtaining 3.83 g of chloroform soluble fraction (fraction 2), and water layer is adjusted to pH 10 with ammonium hydroxide, then extracted 2 times in the same quantities of chloroform:methanol (3:1). The layer dissolved in chloroform:methanol (3:1) is vacuum concentrated and freeze dried to obtain 0.26 g of chloroform:methanol soluble fraction (fraction 3). Water layer is extracted 3 times in the same quantities of methanol, vacuum concentrated and freeze dried to obtain 4.5 of methanol soluble fraction (fraction 4) and 0.65 g of water soluble fraction (fraction 5) respectively, and they are used as a sample in the following activated experiments.

Experiment 1: Grease Gap Assay

1) Experiment Method

The wedges of rat cerebral cortex were prepared and installed in two compartment brain bath to perform an experiment [Harrison N L, Simmonds, M A, Quantitative studies on some antagonists of N-methyl D-aspartate in slices rat cerebral cortex, *Br. J Phamacol.* 84, p381-391, 1985]. The brain was immediately taken out and the 2~3 mm of the fore part was removed using a brain tissue slicer. The remaining part was cut vertically to produce a coronal section in 500~600 μm thick and immediately put in an oxygenated Krebs medium, then bisected in the center of median line to produce wedges in which dorsal cortical surface containing cerebral cortex and corpus callosum was approximately 1.5 mm wide and the ventral surface was approximately 1 mm wide. The wedges were further incubated for 2 hours in an oxygenated Krebs medium at room temperature, and then installed between the slits on which high vacuum silicone grease was applied in two compartment brain bath. The Krebs medium was flowed at the speed of 2 ml per minute through both compartments. Administration of pericarpium zanthoxyli extracts (fractions 1, 2, 3, 4 and 5) with the concentration of 10 µg/ml started in advance in the compartment of cerebral cortex side 10 minutes before, and a excitatory amino acid AMPA (α-amino-3-hydroxyl-5-methyl-4-isoxazolpropionate) 40 µM was administered for 2 minutes. Then, the d.c. potential between the two compartments were monitored via Ag/AgCl electrodes. The signal was amplified and analyzed with the aid of McLab software.

2) Experiment Result

Figure 1B:
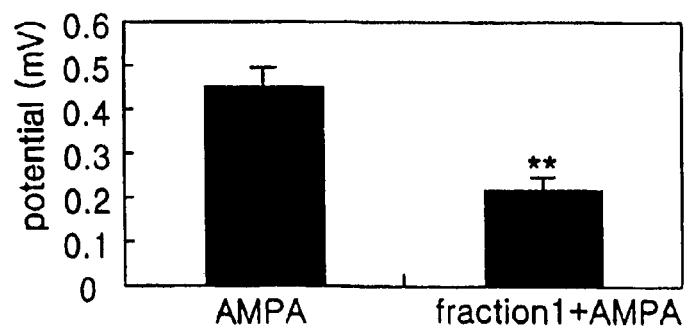
Figure 2:
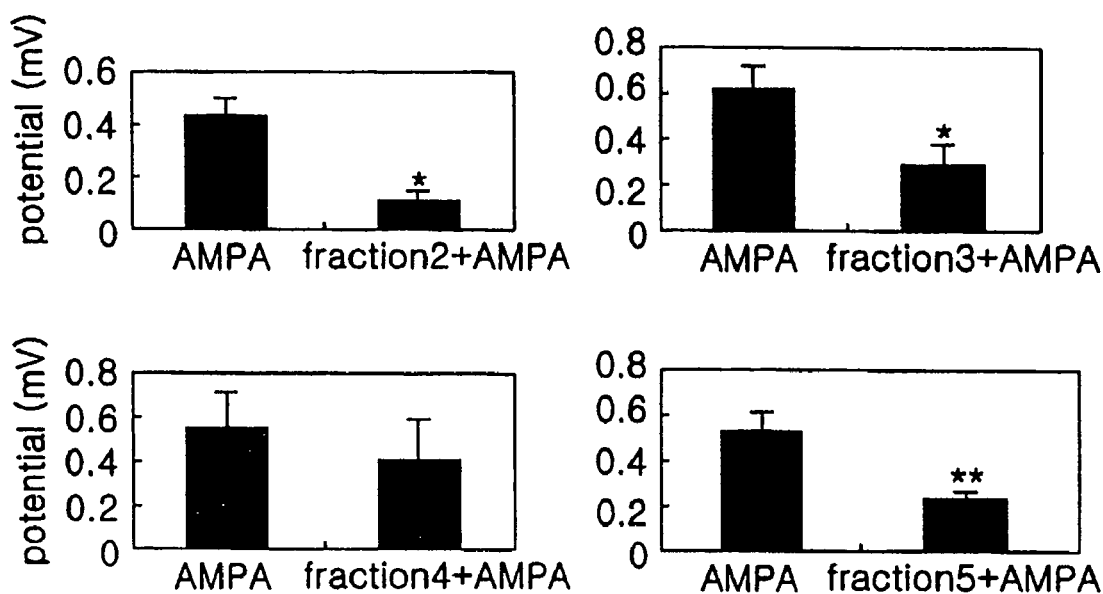
FIG. 2 shows pericarpium zanthoxyli extract (fraction 2, 3, 4 and 5) blocking the depolarization induced by AMPA in the rat cortical slices. Data are expressed as mean±standard deviation (n=5). *: $P<0.05$, **: $P<0.01$ with respect to the control.

Inducing neuron cell depolarization by AMPA is considered as a barometer of stimulation by neuron cell damage. As shown in FIG. 1A, the experimental result revealed that 0.45 mV of depolarization is induced when AMPA 40µM is administered in two compartment brain bath, but on the other hand, the level of depolarization is remarkably reduced to 0.21 mV when AMPA is administered after pretreating the pericarpium zanthoxyli extract (fraction 1) (10 µg/ml) (FIG. 1B). In particular, the result of pretreatment with other fractions of pericarpium zanthoxyli (fractions 2, 3, 4 and 5) revealed that depolarization by AMPA is suppressed by 75%, 54%, 27%, and 67%, respectively (FIG. 2).

Therefore, it is concluded that neuroprotection is induced by various components of pericarpium zanthoxyli extract.

Experiment 2: MTT Assay

1) Experiment Method

MTT assay is a method to measure mitochondrial redox with colorimeter and it is primarily used for examining cell survival rate or mitochondrial redox potential [Mosmann et al., *J. Immonol. Methods.* 65. p55-63, 1983].

In this experiment, to examine cell survival rate, various concentrations of pericarpium zanthoxyli extract were added to each group of cells that had been cultured for 24 hours in a culture media, respectively. MTT reagent (Sigma, USA); 3-[4,5-dimethylthiazol-2-il]-2,5-diphenyl tetrazolium bromide, product number M 2128, was dissolved in PBS (phosphate buffered saline) and filtered, and then finally added to each well at the concentration of 0.5 mg/ml. The cells were further cultured for 3 hours at 37° C. This time, since live cells having active mitochondria decompose tetrazolium ring to form deep blue formazan, 100 µl of DMSO and 10 µl of Sorenson glycine buffer (0.1M glycine, 0.1M NaCl, pH 10.5) were added for the dissolution of it, and then absorption was measured at 570 nm.

2) Experiment Result

Figure 3:
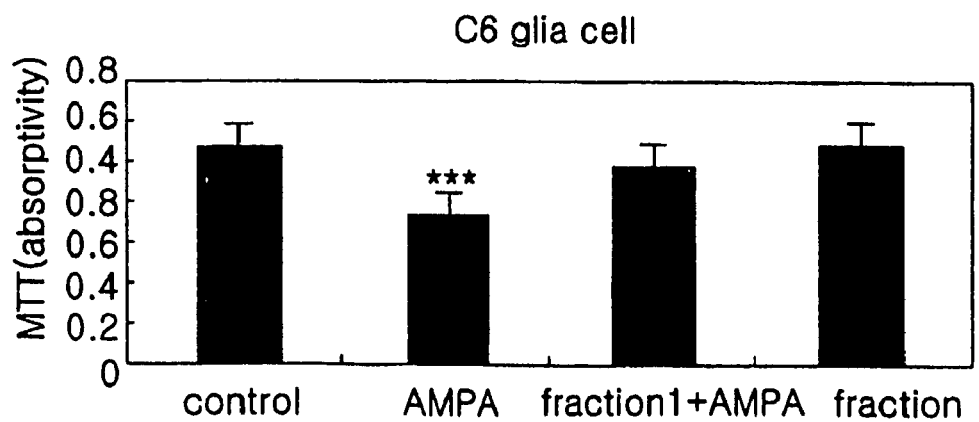
FIG. 3 shows pericarpium zanthoxyli extract (fraction 1) having inhibitory actions against cell damages induced by AMPA in the C6 glial cells. Data are expressed as mean±standard deviation (n=5). ***: $P<0.001$ with respect to the control.

As shown in FIG. 3, the experimental result revealed that approximately 32% of the cells were dead when AMPA (40 µM) was administered to C6 glial cells, but the survival rate of cells was restored to over 90% when a pericarpium zanthoxyli extract (fraction 1) (10 µg/ml) was pretreated.

Experiment 3: $NaNO_2$ Memory Test

It is generally known that cerebral oxygen metabolic deficiency due to $NaNO_2$ and cholinergic nerve conduction, which is related to memory and learning, are closely related each other [Schindler et al., Nootropic drugs: Animal models for studying effects on cognition, *Drug Develop Res* 4: p567-576, 1984]. Cerebral oxidative metabolism disorder due to $NaNO_2$ and memory disorder due to cholinergic neurodepression are closely related each other. Therefore, in case where a delay of death inducing time is shown due to $NaNO_2$ after medication, it can be considered as a index of showing an effect of improving memory by the medication.

1) Experiment Method

A pericarpium zanthoxyli extract (fraction 1) was administered to a male mouse (20 g) at 10 mg/kg, P.O., and after 60 minutes, $NaNO_2$ (250 mg/kg, s.c.) was injected and breath holding time was measured in order to evaluate an effect of improve memory by comparing the breath holding time with the control group.

2) Experiment Result

Figure 4:
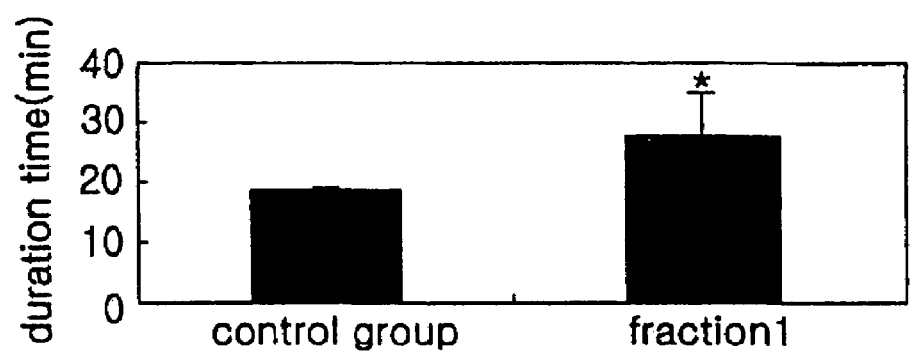
FIG. 4 shows pericarpium zanthoxyli extract (fraction 1) having increased memory in the $NaNO_2$ assay. Data are expressed as mean±standard deviation (n=8). *: $P<0.05$ with respect to the control

As shown in FIG. 4, the experimental result revealed an effect of improving memory by pericarpium zanthoxyli, through increasing death inducing time by 45% when a pericarpium zanthoxyli extract (fraction 1) (10 mg/kg, P.O.) is pretreated, as compared with the death inducing time due to cerebral metabolic disorder by $NaNO_2$.

Experiment 4: Passive Avoidance Test

1) Experiment Method

On a male mouse (20 g), a pericarpium zanthoxyli extract (fraction 1, fraction 2, fraction 3, fraction 4 or fraction 5) was administered for 3 days at 10 mg/kg, P.O. daily, and passive avoidance test was performed using Gemini Avoidance System, San Diego Instruments, USA. The experiment, which is based upon a method of Kumar et al. with some modifications, was performed as follows [Kumar, V., Singh, P. N., Muruganandan, A. V., Bhattacharya, Effect of Indian Hypericum perforatum Linn on animal models of cognitive dysfunction. *J. Ethnopharmacology* 72, p119-128, 2000].

In a first day of training test, a mouse was put in a bright box and acclimated for 300 seconds, and then a door was automatically open to let him into a dark box. When moved into the dark box, an electric stimulus of 0.3 mA was applied for a second. Scopolamine was administered (1 mg/kg, i.p) immediately after termination of the training session. In a second day of retention test after 24 hours, the mouse was put in the bright box and acclimated for 300 seconds, and then the door was open for him to move into the dark box. Then, the time for moving into the dark box was measured. On the day of retention test, an electric stimulus was not applied. If the mouse was not moved into the dark box for 500 seconds, the maximum point 500 seconds was given.

2) Experiment Result

Figure 5A:
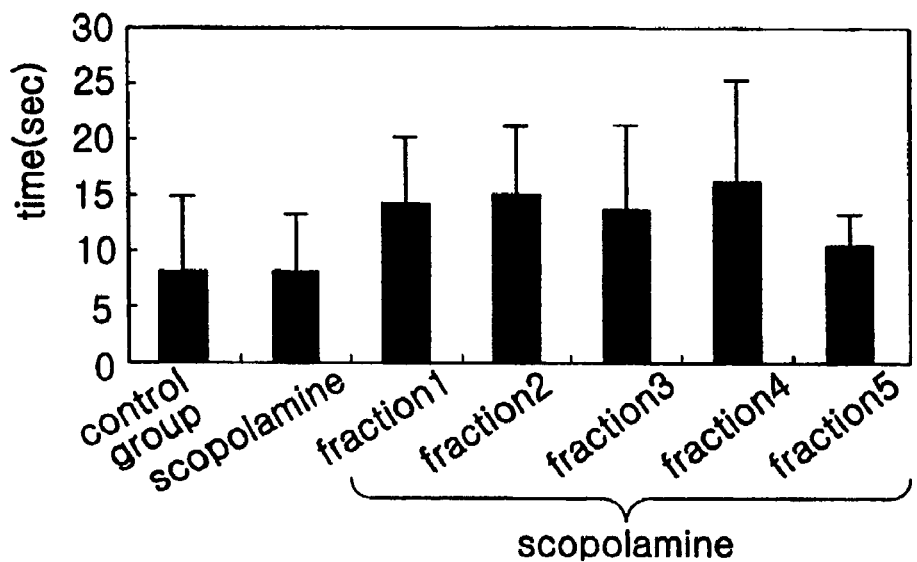
FIG. 5 shows pericarpium zanthoxyli extract (fraction 1, 2, 3, 4 and 5) stimulating memory enhancement in the passive avoidance test. Data are expressed as mean±standard deviation (n=6). *: $P<0.05$, **: $P<0.01$ with respect to the control.
Figure 5B:
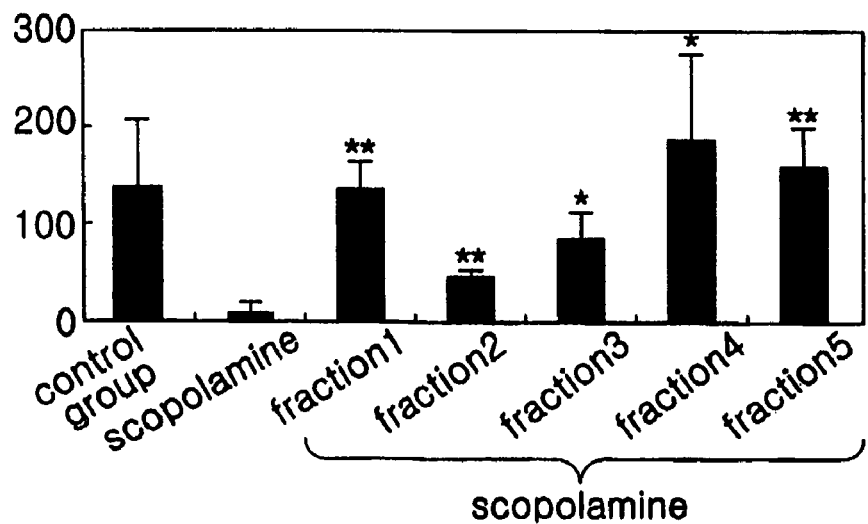

As shown in FIG. 5A, in the first day of training test, there was no significant difference for each test group. As shown in FIG. 5B, in the second day of retention test, for a mouse with dementia induced by scopolamine treatment, memory power was diminished by 92.7% when compared with the control group. However, for a mouse on which a pericarpium zanthoxyli fraction 1, 2, 3, 4 or 5 was administered for 3 days, memory disorder due to scopolamine was restored by 99%, 33%, 61%, 133% or 112%, respectively, showing an excellent effect of improving memory power.

Experiment 5: Oral Toxicity Test of Pericarpium Zanthoxyli Extracts

1) Experiment Method

25 ICR mice in the weight of about 20 g were bred in an animal room at 23° C., relative humidity 50%, illuminance 150~300 lux for a week, and then divided into 5 groups each comprising of 5 mice for testing.

A pericarpium zanthoxyli extract (fraction 1, fraction 2, fraction 3, fraction 4 or fraction 5) obtained from the example was dissolved in 0.1% Tween 80, and then the 100 times (1,000 mg/kg, P.O.) –1000 times (10,000 mg/kg, P.O.) of the action-inducing dosage (10 mg/kg, P.O.) was orally administered once to 5 groups of mice, respectively. After the administration, changes of general symptoms and existence of animal death were checked for 7 days. On the 7th day of administration the mice were killed and dissected for examining viscera with the naked eye.

2) Experiment Result

Abnormal findings due to administering a fraction of pericarpium zanthoxyli were not observed, and the lethal dosage of a pericarpium zanthoxyli extract for fraction 1, fraction 2, fraction 3, fraction 4 and fraction 5 was shown as over 5,000 mg/kg, over 10,000 mg/kg, over 10,000 mg/kg, over 5,000 mg/kg and over 5,000 mg/kg respectively.

Hereinafter, pharmaceutical preparations for the composition will be described, but they are not meant to restrict this invention, and are only for expatiation.

Pharmaceutical Preparation 1: Tablet

According to a general method of producing tablets, each tablet of the composition below was pharmaceutically prepared.

| Methanol extract of pericarpium zanthoxyli | 500.0 mg |
|---|---|
| Lactose | 500.0 mg |
| Talc | 5.0 mg |
| Magnesium stearate | 1.0 mg |

Pharmaceutical Preparation 2: Capsule

According to the following method, each capsule of the composition below was pharmaceutically prepared.

An extract of pericarpium zanthoxyli was sifted out and mixed with an excipient, and then filled into a gelatin capsule to produce a capsule.

| Methanol extract of pericarpium zanthoxyli | 500.0 mg |
|---|---|
| Starch 1500 | 10.0 mg |
| Magnesium stearate | 100.0 mg |

Pharmaceutical Preparation 3: Syrup

According to the following method, syrup of the composition below was pharmaceutically prepared.

First, white sugar was dissolved in purified water. Paraoxybenzoate, paraoxypropylbenzoate and pericarpium zanthoxyli extract were added, and dissolved at 60° C. and then cooled down, and purified water was added for producing 150 ml.

| Methanol extract of pericarpium zanthoxyli | 5.0 g |
|---|---|
| White sugar | 95.1 g |
| Paraoxybenzoate | 80.0 mg |
| Paraoxypropylbenzoate | 16.0 mg |
| Purified water | to 150 ml |

Pharmaceutical Preparation 4: Liquid Formulation

According to a general method of producing liquid formulation, a liquid formulation of the composition below was pharmaceutically prepared, and filled into an amber colored bottle.

| Methanol extract of pericarpium zanthoxyli | 500.0 mg |
|---|---|
| Isomeric sugar | 20.0 g |
| Antioxidant | 5.0 mg |
| Methyl paraoxybenzoate | 2.0 mg |
| Purified water | to 100.0 ml |

Pharmaceutical Preparation 5: Powder

According to a general method of producing powder, a powder of the composition below was pharmaceutically prepared, and filled into a packet and sealed up.

| Methanol extract of pericarpium zanthoxyli | 50.0 mg |
|---|---|
| Lactose | 100.0 mg |
| Talc | 5.0 mg |

Pharmaceutical Preparation 6: Injection

According to a general method of producing injections, they were pharmaceutically prepared, and filled into an ampoule of capacity 2.0 ml shown as the composition below, and then sterilized.

| Methanol extract of pericarpium zanthoxyli | 50.0 mg |
|---|---|
| Antioxidant | 1.0 mg |
| Tween 80 | 1.0 mg |
| Distilled water for injections | to 2.0 ml |

Moreover, health foods were produced as described in the following method.

Brown rice, barley, jobs tear were gelatinized, dehydrated and distributed in a commonly known method for producing powder in the fineness of mesh 60 using a grinder. Moreover, black bean, black sesame and perilla were steamed, dehydrated and distributed in a commonly known method for producing powder in the fineness of mesh 60 using a grinder.

The grains, fruits and dried pericarpium zanthoxyli extract, which had been produced as described above, were mixed in the following ratio for producing granules.

[Grains: brown rice 30 weight %, jobs tear 15 weight %, barley 20 weight %; Fruits: perilla 7 weight %, black bean 8 weight %, black sesame 7 weight %; Dried powder of pericarpium zanthoxyli extract: 3 weight %, bracket fungus 0.5 weight %, geogen 0.5 weight %]

Owing to the function of protecting brain cells resulting from an extract of pericarpium zanthoxyli, the composition containing an extract of pericarpium zanthoxyli shows not only an effect of preventing and treating degenerative cerebral disorders, but also an effect of inducing memory improvement. It has the function of protecting brain cells for modern people, suffering brain damage caused by various environmental stresses, and therefore it can be used for the persons whose memory power has been deteriorated, such as dementia patients.

The invention claimed is:

1. A method for protecting brain cells from excitotoxicity and for improving memory, wherein the method comprises administering to a mammal in need thereof a composition comprising an extract of pericarpium zanthoxyli contained in a designated fraction obtained by the process of:

a) extracting pericarpium zanthoxyli in an organic solvent chosen from i) a low alcohol having 1-4 carbon atoms; ii) acetone; iii) chloroform; iv) methylene chloride; v) ether; vi) ethyl acetate; vii) mixtures of (i)-(vi); or viii) a mixed solvent of a low alcohol having 1-4 carbon atoms and water, thereby obtaining a first fraction (fraction 1) comprising the solvent;

b) combining the first fraction of step (a) with a mixed solvent of a low alcohol having 1-4 carbon atoms and water to obtain a mixture;

c) adjusting the pH of the mixture of step (b) to 2 to 4; and d) further extracting the mixture of step (c) with an equal volume of chloroform, thereby obtaining a chloroform soluble fraction (fraction 2) and a water layer.

2. The method according to claim 1, wherein the composition comprises 0.5-50 weight % of pericarpium zanthoxyli extract against total weight of the composition.

3. The method according to claim 1, wherein the process for obtaining an extract of pericarpium zanthoxyli further comprises:

e) adjusting the pH of the water layer of step (d) to pH 9-12, and f) extracting and fractionating the pH adjusted water layer of step (e) with an equal volume of a chloroform:methanol mixed solvent, thereby obtaining a chloroform:methanol soluble fraction (fraction 3) and a second water layer.

4. The method according to claim 3, wherein the process for obtaining an extract of pericarpium zanthoxyli further comprises:

g) extracting and fractionating the second water layer obtained in step (f) with methanol thereby obtaining a methanol soluble fraction (fraction 4) and a water soluble fraction (fraction 5).

5. The method according to claim 1, wherein the composition further comprises carriers, excipients, diluents or a mixture thereof.

6. The method according to claim 1, wherein the composition is provided in oral, external or suppository form or as a sterile injectable solution.

7. The method according to claim 1, wherein the composition is provided in a food or drink.

8. The method according to claim 1, wherein the organic solvent step (a) is a mixed solvent of low alcohol having 1-4 carbon atoms and water.

9. The method according to claim 8, wherein the solvent of a low alcohol having 1-4 carbon atoms is methanol.

10. The method according to claim 9, wherein the ratio of methanol:water in step (a) is in a range of 1:0.2 to 1:1.5.

11. The method of claim 1, wherein extraction steps (a) and (d) are performed more than one time.

12. The method of claim 1, wherein step (a) is performed at a temperature in the range of 5° C. to 80° C.

13. The method of claim 12, wherein the temperature is 30° C. to 55° C.

14. The method of claim 1, wherein the reaction time for performing step (a) is in a range of 15 minutes to 48 hours.

15. The method of claim 14, wherein the reaction time is 30 minutes to 12 hours.

16. The method of claim 1, wherein the solvent of a low alcohol having 1-4 carbon atoms in step (b) is methanol.

17. The method of claim 16, wherein the ratio of methanol:water in step (b) is 1:0.5 to 1:1.5.

18. The method of claim 1, wherein in step (c) the pH is adjusted by adding sulfuric acid.

19. The method of claim 3, wherein in step (e) the pH is adjusted by adding ammonium hydroxide.

20. The method of claim 1, wherein the composition is provided in a dosage range of 0.1 mg/kg to 500 mg/kg.

21. The method of claim 20, wherein the composition is provided in a dosage range of 10 mg/kg.

22. The method of claim 7, wherein the amount of pericarpium zanthoxyli extract provided in the food is in the range of 0.1 to 15of weight of the total weight of the food.

23. The method of claim 22, wherein the amount of pericarpium zanthoxyli extract provided in the food is from 1 to 10% weight of the total.

24. The method of claim 7, wherein the amount of pericarpium zanthoxyli extract provided in the drink is in the range of 1 g to 30 g per 100 ml of the drink.

25. The method of claim 24, wherein the amount of pericaprium zanthoxyli extract provided in the drink is from 3 g to 10 g per 100 ml of the drink.

26. The method according to claim 3, wherein the administering step comprises administering a composition comprising an extract of pericarpium zanthoxyli contained in fraction 3.

27. The method according to claim 4, wherein the administering step comprises administering a composition comprising an extract of pericarpium zanthoxyli contained in fraction 4 or 5.

* * * * *

UNITED STATES PATENT AND TRADEMARK OFFICE
CERTIFICATE OF CORRECTION

| | | |
|---|---|---|
| PATENT NO. | : 7,514,104 B2 | Page 1 of 1 |
| APPLICATION NO. | : 11/283635 | |
| DATED | : April 7, 2009 | |
| INVENTOR(S) | : Sung Jin Kim | |

It is certified that error appears in the above-identified patent and that said Letters Patent is hereby corrected as shown below:

On the Title Page:

Item (63) Related U.S. Application Data, line 3, delete "PCT/KR02/02061" and replace with --PCT/KR02/00261--.

Item (57) ABSTRACT, line 2, delete "pericapium" and replace with --pericarpium--.

Column 7:

Line 27, delete "(10 μg/ml)" and replace with --(10μ/ml)--.

Column 12:

Line 24, Claim 20, line 2, after mg/kg, add --body weight--.

Line 26, Claim 21, line 2, after mg/kg, add --body weight--.

Line 29, Claim 22, line 3, delete "0.1 to 15of" and replace with --0.1% to 15% weight--.

Line 31, Claim 23, line 2, delete "1" and replace with --1%--.

Signed and Sealed this

Twenty-third Day of June, 2009

JOHN DOLL
*Acting Director of the United States Patent and Trademark Office*